US00PP22859P3

(12) United States Plant Patent

Schmider et al.

(10) Patent No.: US PP22,859 P3

(45) Date of Patent: Jul. 17, 2012

(54) APPLE TREE NAMED 'GOLDEN PARSI'

(50) Latin Name: *Malus domestica Borkh*
Varietal Denomination: Golden Parsi

(75) Inventors: Egon Schmider, Algund (IT); Thomas Braun, Girlan/Eppan (IT)

(73) Assignee: Kikli SRL-GmbH, Girlan/Eppan (IT)

( * ) Notice: Subject to any disclaimer, the term of this patent is extended or adjusted under 35 U.S.C. 154(b) by 0 days.

(21) Appl. No.: 12/798,834

(22) Filed: Apr. 13, 2010

(65) Prior Publication Data

US 2011/0252514 P1 Oct. 13, 2011

(51) Int. Cl.
*A01H 5/00* (2006.01)

(52) U.S. Cl. ..... Plt./172; Plt./161

(58) Field of Classification Search ..... Plt./172, Plt./161

See application file for complete search history.

*Primary Examiner* — June Hwu

*Assistant Examiner* — Louanne Krawczewicz Myers

(74) *Attorney, Agent, or Firm* — Horst M. Kasper

(57) ABSTRACT

The present invention relates to a variety of an apple tree obtained by branch mutation and by selection of the variety 'Golden Clone B'. The present invention variety 'Golden Parsi' exhibits an appropriate distinguishability, homogeneity, uniformity, and stability. The vigor of the tree is medium. The tree type is ramified. The habit of the apple tree is spreading. The pubescence on an upper half of a shoot is weak or similar to the pubescence in 'Golden Delicious'. The thickness as measured by the diameter at the center is medium or similar to the thickness in 'Jonagold' for a one year old shoot. The number of lenticels is many for a one year old shoot. The predominant color of a flower is dark pink in a balloon stage. An overcolor appears early in season with a brown-red color. The overcolor disappears almost totally, and toward harvest increases and gets red. The overcolor remains red even after months of storage.

6 Drawing Sheets

Latin name of the genus of the plant claimed: *Malus*.

Latin name of the species of the plant claimed: *domestica* Borkh.

Variety denomination: 'Golden Parsi'.

BACKGROUND OF THE INVENTION

1. Field of the Invention

The present invention relates to a novel apple tree.

2. Brief Description of the Background of the Invention Including Prior Art

A known variety of an apple plant is *Malus domestica*. A variety of *Malus domestica* is called 'Golden Clone B'. Another variety of *Malus domestica* is called 'Golden Reinders'.

BRIEF SUMMARY OF THE INVENTION

A vegetatively propagated variety of *Malus domestica* is designated 'Golden Parsi'. The variety has been bred by a naturally occurring tree mutation of the variety 'Golden Clone B' by selection such that the variety 'Golden Parsi' exhibits a necessary distinguishability, homogeneity, uniformity, and stability.

DETAILED BOTANICAL DESCRIPTION

Figure 1:
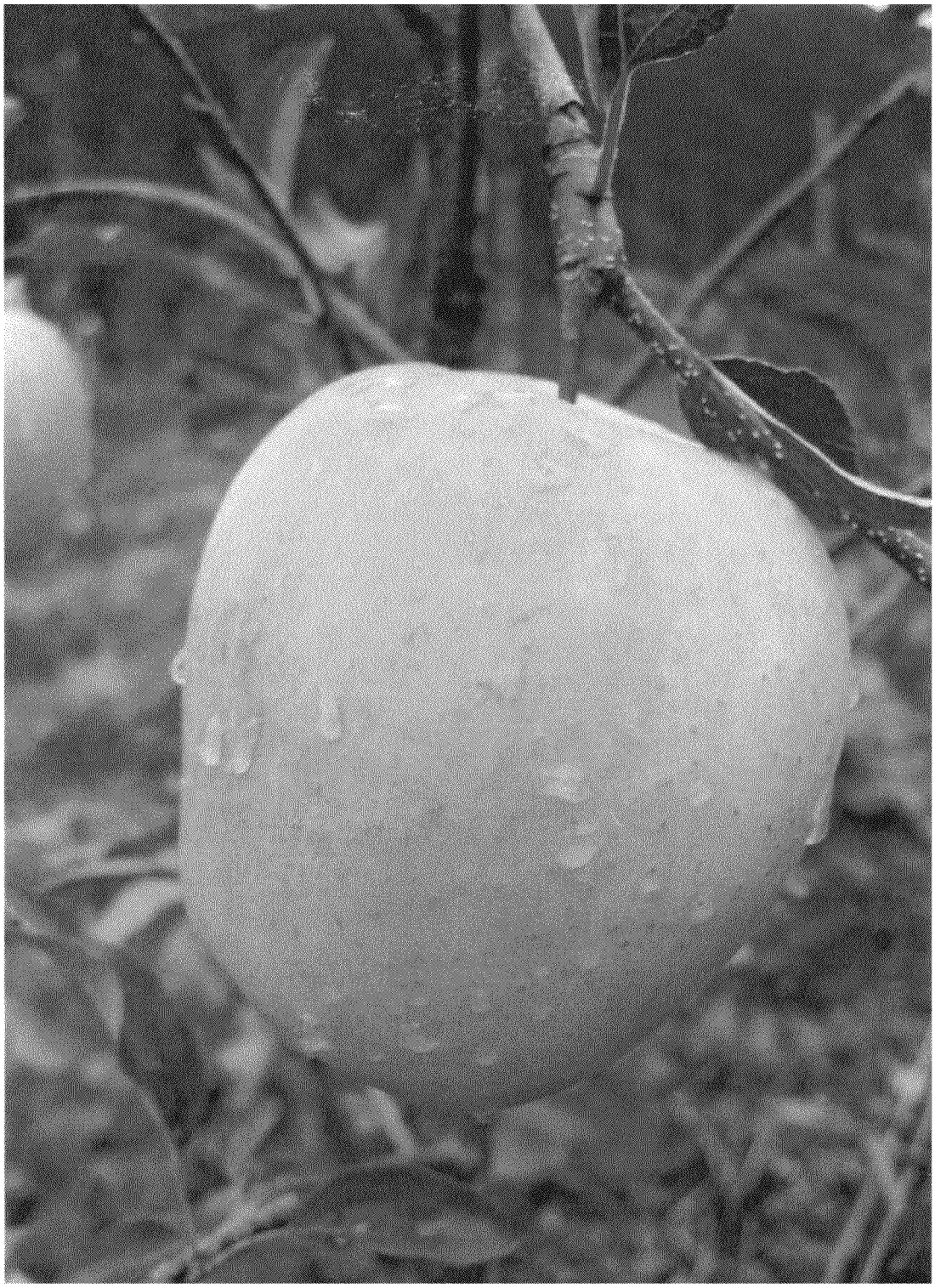
FIG. 1 is a front side elevational view of a fruit of the apple tree 'Golden Parsi'.
Figure 2:
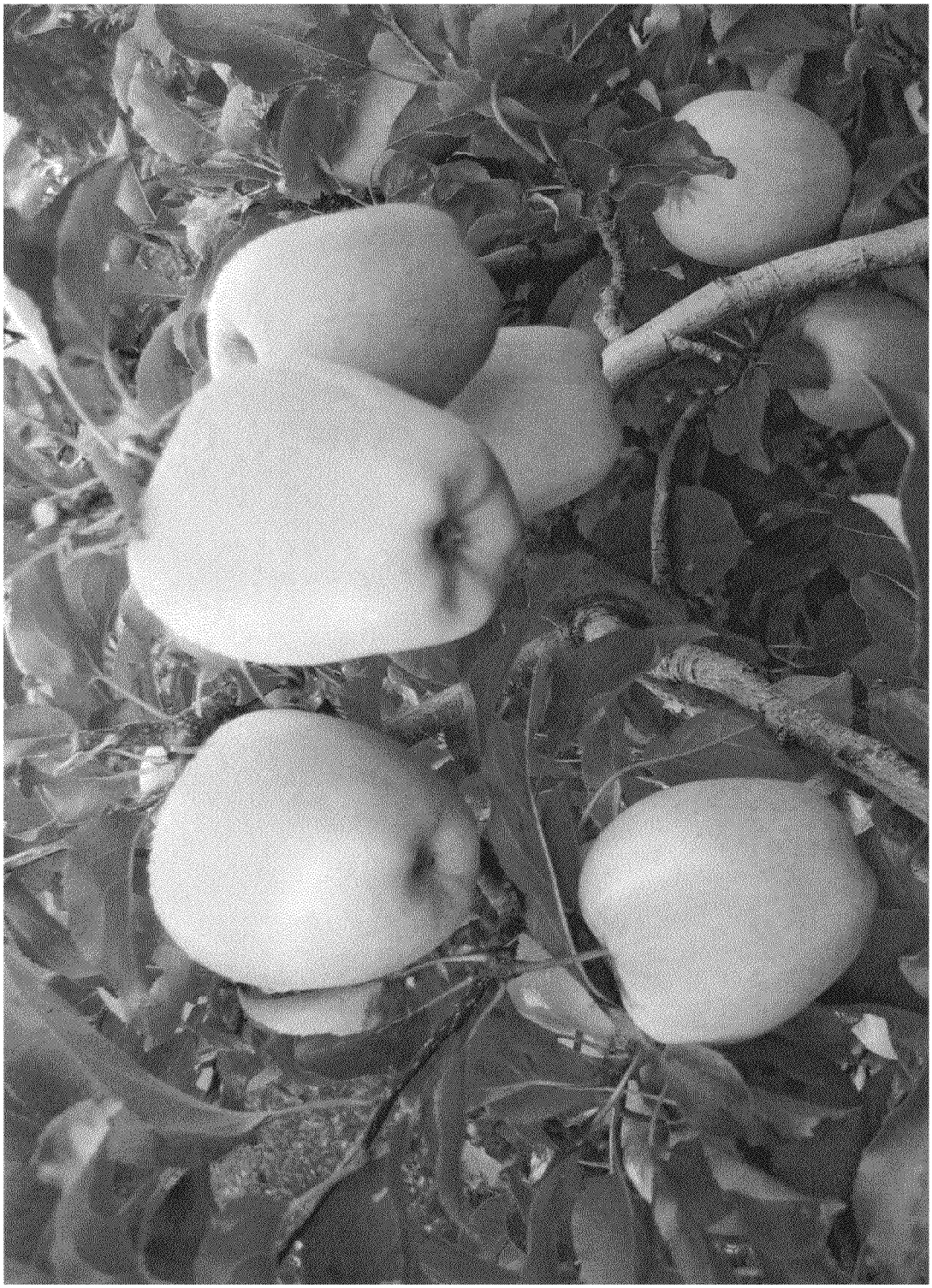
FIG. 2 is a view of several fruits of an apple tree 'Golden Parsi'.
Figure 3:
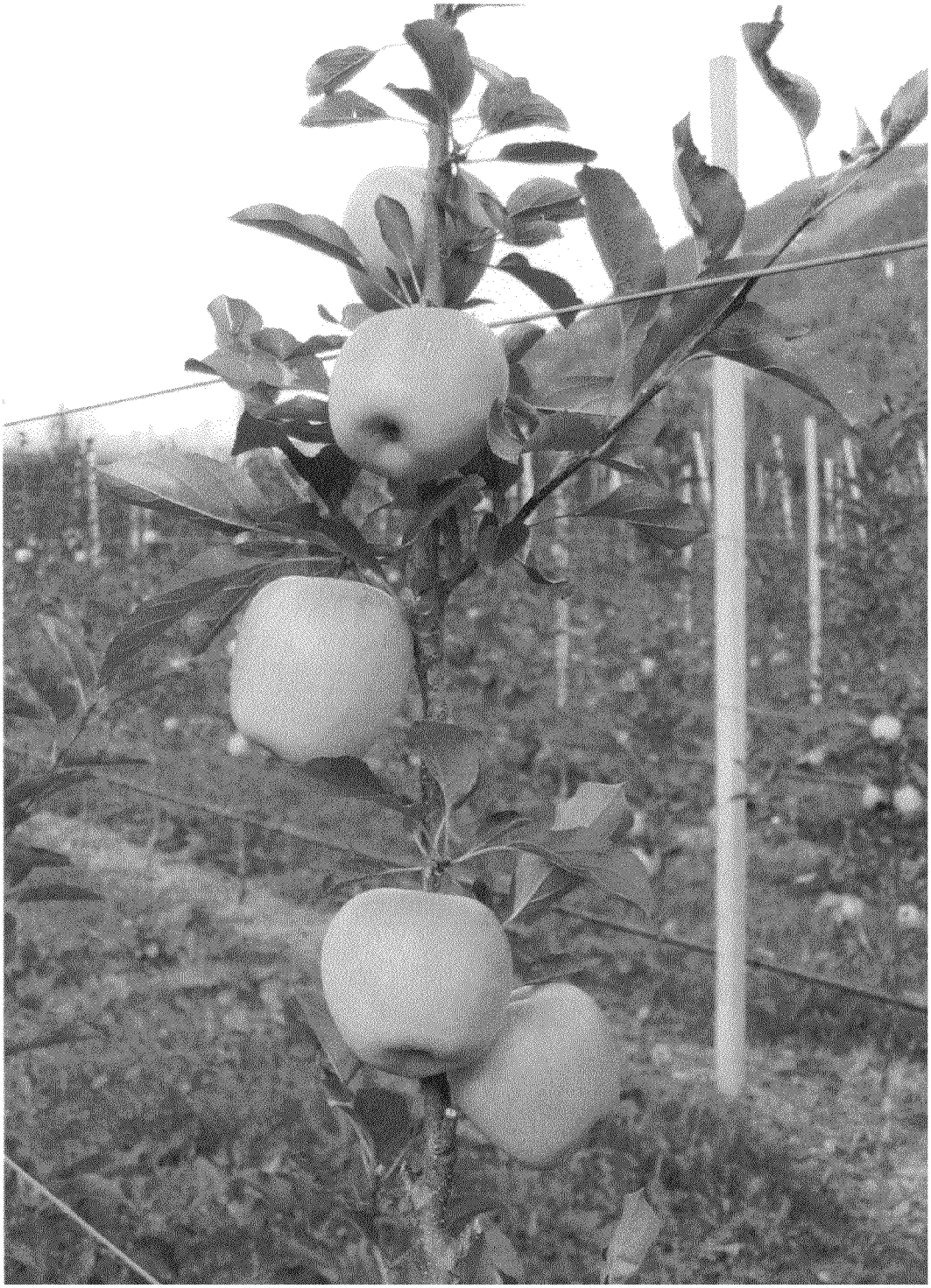
FIG. 3 is a side elevational view of fruits hanging on an apple tree 'Golden Parsi'.
Figure 4:
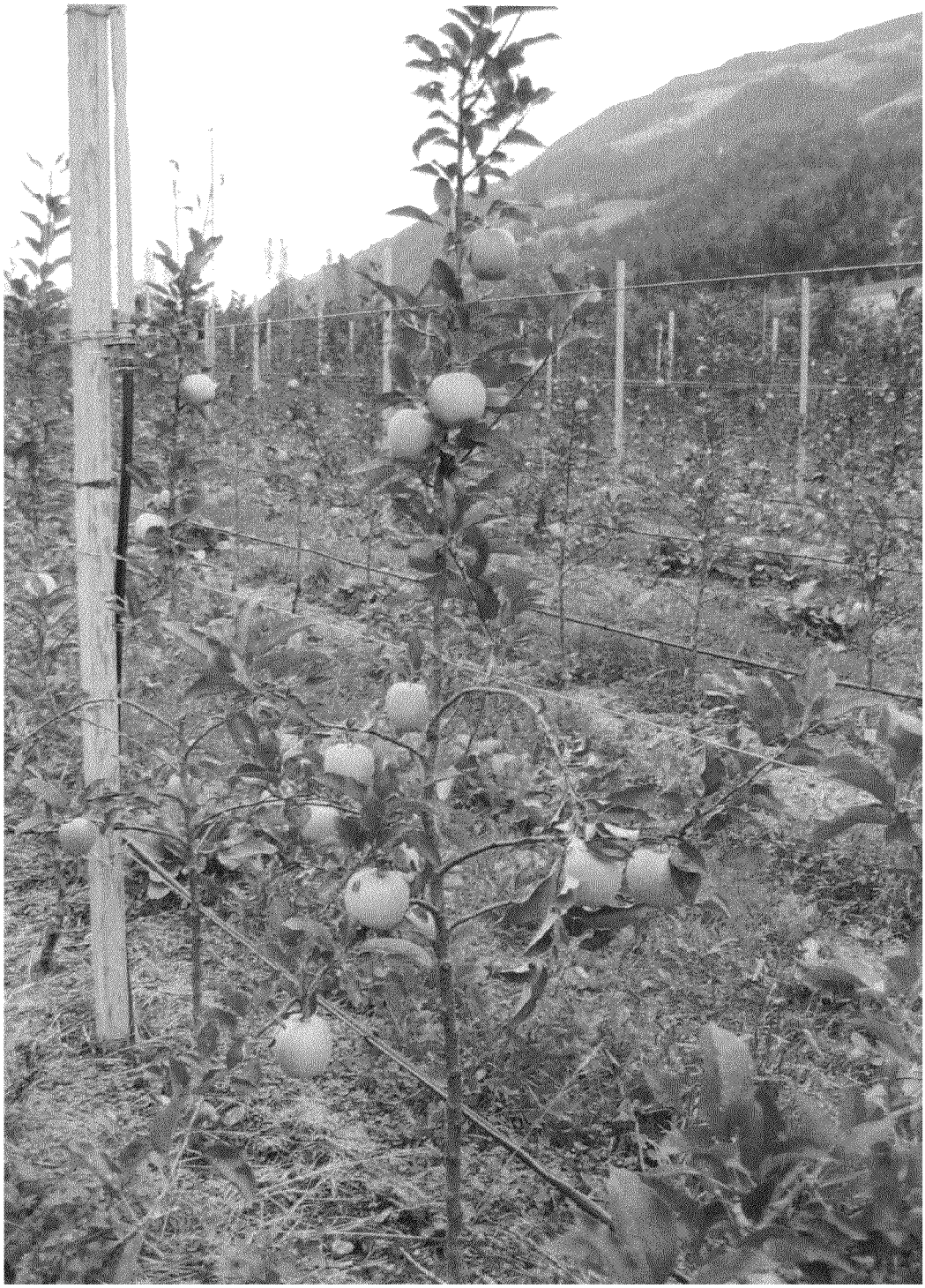
FIG. 4 is a perspective view of a field with 'Golden Parsi' trees.
Figure 5:
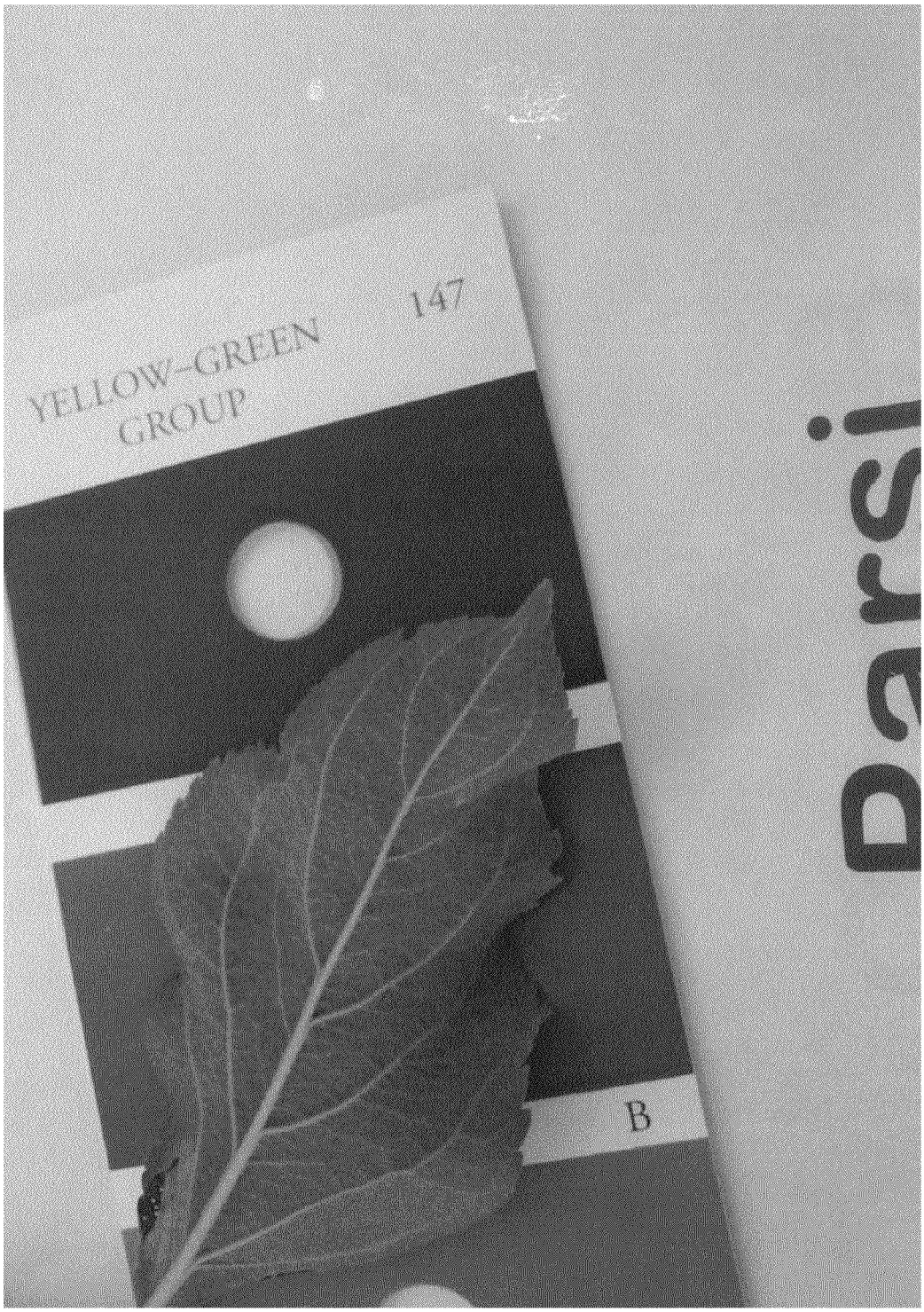
FIG. 5 is a bottom view onto a leaf of a 'Golden Parsi' tree.
Figure 6:
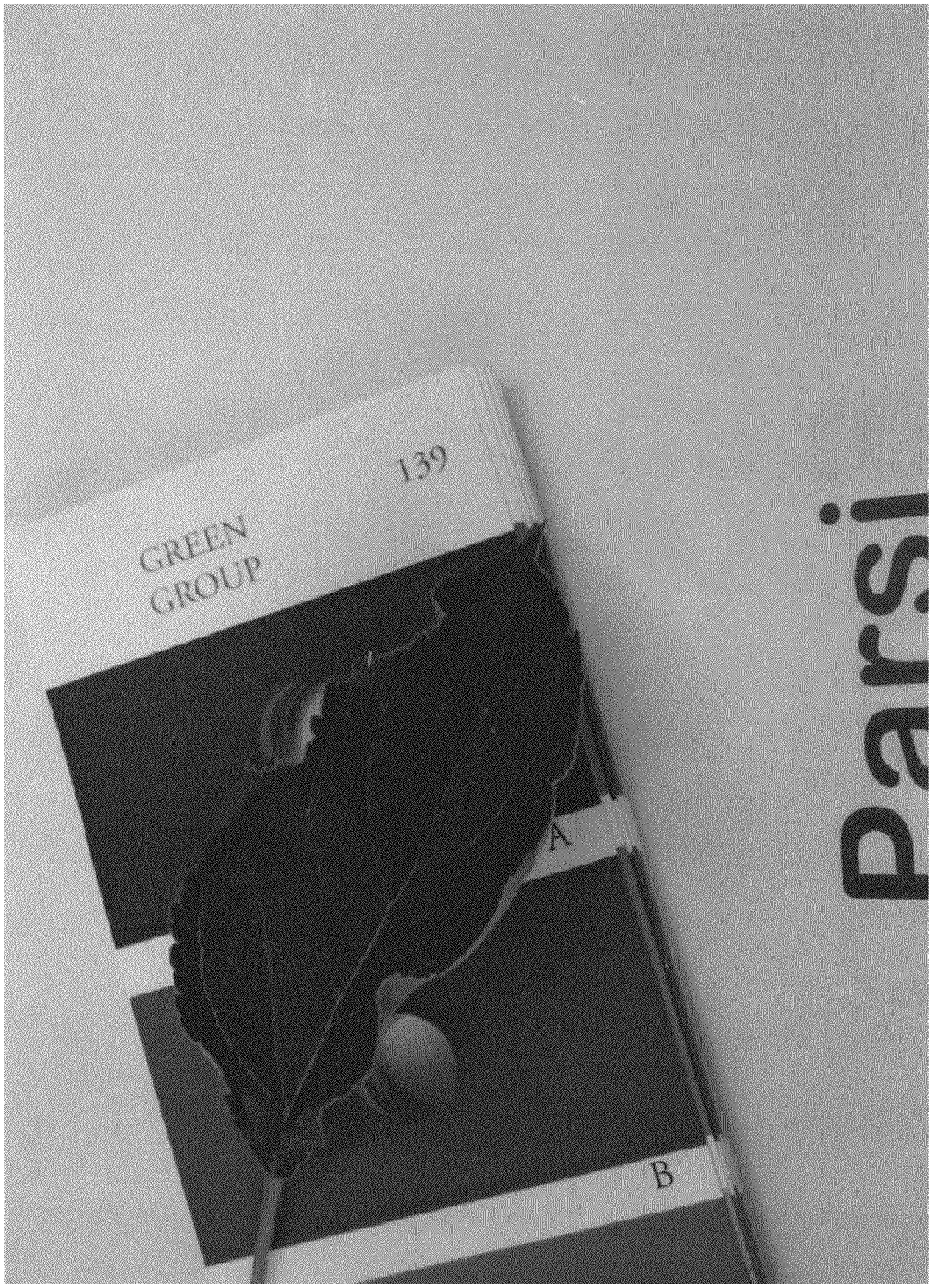
FIG. 6 is a top view onto a leaf of a 'Golden Parsi' tree.

The present invention relates to a variety of an apple tree. A naturally occurring tree mutation 'Golden Parsi' of the variety 'Golden Clone B' has been discovered and found by selection such that the present invention variety exhibits an appropriate distinguishability, homogeneity, uniformity, and stability.

A brief comparison between the parental cultivar 'Golden Clone B' and the instant plant 'Golden Parsi' is now presented. The 'Golden Parsi' fruit exhibits a blush, which appears early in the season, in June, with a brown red color. The blush disappears almost totally, and toward harvest increases and gets red FAN1 (red) 39A. The blush remains red even after months of storage. The 'Golden Clone B' does not show such blush. The crowning of the fruit of the 'Golden Clone B' is small at the calyx end, whereas the crowning of the fruit of 'Golden Parsi' is very dominant at the calyx end. The russet of the fruit is high on the 'Golden Clone B', whereas the russet on the fruit of the 'Golden Parsi' is absent or very low. The russet around the stalk cavity of the fruit of the 'Golden Clone B' is medium, whereas the russet around the stalk cavity of the fruit of the 'Golden Parsi' is absent or very low. The russet on the fruit of the 'Golden Clone B' around the eye basin is medium, whereas the russet on the fruit of the 'Golden Parsi' around the eye basin is absent or very low. The russet on the cheeks of the fruit of the 'Golden Clone B' is medium, whereas the russet on the cheeks of the fruit of the 'Golden Parsi' is absent or very low.

The original 'Golden Parsi' tree was found in a fruit plantation located in South Tyrol, Italy. Asexual production occurred in Presina near Verona, Italy. Consideration was given to the stability of propagation. The tree 'Golden Parsi' exhibits a 100 percent variety originality in commercial installations. The so-called regression rate or reversion rate is zero. The typical properties of 'Golden Parsi' did not change in the course of propagation. The properties were observed on 2, 3, and 4 year old trees. In case there are other values of the age of the trees, then these values are specified. The observed plant retains its distinctive characteristics and reproduces true to type in successive generations. 'Golden Parsi' is reproduced by chip budding.

The vigor of the 'Golden Parsi' tree is medium and similar to the vigor of 'Golden Delicious'. The height of a tree of 'Golden Parsi' in third year with leaves after planting is from about 220 cm+−20 cm. The height of a tree of 'Golden Parsi' in fourth year with leaves after planting is from about 240 cm+−20 cm. The diameter of the trunk of a 'Golden Parsi' tree in third year with leaves after planting is 25 cm+−0.2 cm. The trunk diameter was measured at a height level of 70 cm above the soil. The diameter of the trunk of a 'Golden Parsi' tree in fourth year with leaves after planting is 29 cm+−0.3 cm. The tree type is ramified similar to the ramification of 'Elstar' or 'Golden Delicious'. The habit of the 'Golden Parsi' apple tree is spreading similar to 'Jonagold' or 'Bramley's Seedling'. Side branches of the 'Golden Parsi' tree start at a height level of 50 cm+−5 cm and reach up to the top of the trunk. The spread is in a ratio of 2 (height): 1 (spread) on all observed trees. The length of the branches of a tree in third year with leaves after planting is from about 30 to 50 cm and the diameter is 0.8 to 1 mm. The length of the branches of a tree in fourth year with leaves after planting is from about 30 to 60 cm and their diameter is from 0.8 to 1.4 mm. The angle of the branches of both trees in third and fourth year is from about 45 to 90 degrees. The angle is 90 degrees on branches at the bottom and becomes smaller toward the top. The attitude of the leaf blade relative to a shoot is upwards or similar to 'Katja' or 'Redsleeves'.

The length of a leaf blade of a 'Golden Parsi' tree is long or similar to the length in 'Bramley's Seedling'. The length of a leaf of a three year old 'Golden Parsi' tree is 9+−3 cm. The length of a leaf of a four year old tree is 9.5+−1 cm. The width of a leaf blade of a 'Golden Parsi' tree is medium or similar to the width in 'Jonagold'. The width of a leaf of a three year old tree is 4+−1 cm. The width of a leaf of a four year old "Golden Parsi" tree is 4.5+−1 cm. The ratio length/width of a leaf blade of a 'Golden Parsi' tree is large or similar to the length/width ratio of a leaf blade in 'Granny Smith'. The ratio of the length to the width of a broad leaf disposed near the stem of a three year old tree 'Golden Parsi' is from about 1.6 to 2. The broad leaves of 'Golden Parsi' disposed near the stem have 40 to 50 serrations on each of the two sides of the leaf. The elongated leaves disposed in the end regions of the shoots have about 30 serrations on each of two sides of the leaf and a total of about 60 to 80 serrations for the whole elongated leaf.

The leaves of 'Golden Parsi' have the following properties: The color of the topside of the leaf is FAN3 green 139A for younger trees. The color on the top side of the leaf is very dark FAN3 green 139A for elder trees. The color of the bottom side of the leaf is FAN3 yellow-green 147B for younger trees. The color of the bottom side of the leaf is FAN3 yellow-green 147B for elder trees. The ratio of the length to the width of a broad leaf disposed near the stem is from 1.6:1 to 2 to 1. The ratio of the length to the width of an elongated leaf disposed in an end region of a shoot is about 1.6 to 1.8:1. The leaf of the 'Golden Parsi' has veins and there are on each side of the leaf 3 to 5 veins. The color of the veins on the bottom side of the leaf is FAN3 yellow-green 145C, the color is darker towards the upper side to FAN 3 yellow-green 145A. The ratio of the length of the leaf (without petiole) to the length of the petiole is 2.9 to 3.3: 1. The transition from the wood to the leaf has the color FAN4 grey-orange 166A.

The intensity of the green color of the top side of the leaf of 'Golden Parsi' is dark or similar to the intensity in 'Mutzu'. The incisions of margin in the upper half of the leaf blade of the 'Golden Parsi' tree are serrate type 1 or are similar to the incisions of 'Elstar' or 'Gala'.

The pubescence on a lower side of a leaf blade of 'Golden Parsi' is absent or weak or similar to the pubescence in 'Golden Delicious'. The length of the petiole of the 'Golden Parsi' tree is long or similar to the length in 'Falstaff'. The color of the petiole is FAN3 yellow-green 145A. The length of a petiole or leafstalk of a three year old tree is from about 2.5 to 3.5 cm. The extent of anthocyanin coloration starting from the base of the petiole of 'Golden Parsi' is medium or similar to the extent in 'Discovery' or 'Richared Delicious'. Each petiole of 'Golden Parsi' carries two stipules. The length of the stipules of 'Golden Parsi' is 0.4 to 0.8 mm. The width of the stipule is 0.05 to 0.1 mm. The color of the stipule is FAN3 yellow-green 145A. The pubescence on an upper distal half of a one-year-old shoot is weak similar to 'Golden Delicious'. The thickness of a one-year-old shoot as measured by the diameter at the center is medium and similar to 'Jonagold' for a one year old shoot. The length of the internode of 'Golden Parsi' is medium and similar to 'Jonagold' or 'Redaphough' for a one year old shoot. The length of an internode for a one year old shoot is 3.5 cm+−0.5 cm. The color on the sunny side of a one year old shoot of 'Golden Parsi' was FAN4 grey-brown N199B like 'Ingrid Marie'. The number of lenticels of a one year old dormant shoot of 'Golden Parsi' was many and similar to the number of lenticels of 'Mutzu', i.e. 25+−5 per square centimeter. The shape of the lenticels of 'Golden Parsi' ranges from dot like/circular to globular/flattened. The lenticels on the trunk have a length of up to 2.5 mm and have a height from 1 to 1.5 mm. In contrast, the length of the lenticels on the branches are only from about 1.0 to 1.5 mm and are therefore smaller. The color of the lenticels on the trunk and on the branches is FAN4 161 B (greyed-yellow group).

The diameter of a flower of 'Golden Parsi' with petals pressed into a horizontal position as seen from above is medium and similar to 'Cox's Orange Pippin'. The predominant color of the petal of 'Golden Parsi' in the balloon state is dark pink and similar to the color of the petal of 'Elstar' or 'Sylvia'. The number of the petals of 'Golden Parsi' is 5. The length of a petal is about 23 mm+−2 mm. The width of a petal is about 15.5 mm+−1 mm. The ratio of the length to the width of the petal of the "Golden Parsi" is about 2 to 1. The diameter of a flower as seen from above is about 52 mm+−2 mm. The petals of the 'Golden Parsi' have light veins and are delicately subdivided.

The upper side of the petals of the 'Golden Parsi' is colored white and the lower side of the petals is colored light pink. The petals of the open flower exhibit a color FAN4 White N155B plus slight traces of FAN2 red-purple 68C on the inside. The petals of the open flower exhibit a color FAN4 white N155B plus slight traces of FAN2 red-purple N66D on the outside. The color of an unopened flower is dark pink in a balloon stage. The size of the flowers of 'Golden Parsi' as measured by the diameter of the flower with petals pressed into a horizontal position is medium. The relative position of the margin of the petals is touching. The main flower on terminal buds had a flowering time of eight days. The after flowering on one year old wood lasted 10 days.

The properties of the flowers of 'Golden Parsi' are as follows: Flowers at balloon stage have color FAN2 red-purple 60A. The flowers are average sensitive and average resistant against unfavorable weather conditions and freezing. The time of flowering of 'Golden Parsi' is from April 14, to April 30 in South Tyrol depending on the climate. The duration of flowering of 'Golden Parsi' is the same as has 'Golden'. The time of duration from the flowering to the harvest is 150 days. All other 'Goldens' compared to 'Golden Parsi' ('Golden Clone B', 'Golden Smoothee', Golden Reinders) show the same characteristics regarding flowering. The flower buds of the 'Golden Parsi' have a diameter of 0.5+–0.2 mm, and a length of 0.5+–0.2 mm, The form of the flower buds of 'Golden Parsi' is exactly the same as that of 'Golden Delicious'. The color of the flower buds of 'Golden Parsi' is FAN4 grey-brown 199B. The flower type and habit of the 'Golden Parsi' were from 5 to 7 flowers per cluster. The flower of the 'Golden Parsi' produces a fragrance. The arrangement of petals in the flower of 'Golden Parsi' is intermediate and similar to that of 'Golden Delicious', 'Jonagold' or 'Topaz'. A flower of 'Golden Parsi' consists of five carpels, each with two ovules and five sepals, petals and styles. The reproductive organs (filaments) have a length of 10+–2 mm. Filaments are erect and number approximately 20. The color of the filaments of 'Golden Parsi' is FAN4 grey-green 193D. The position of stigmas relative to anthers in 'Golden Parsi' is above and similar to 'Golden Delicious'.

The pollen of the 'Golden Parsi' flower has a color of FAN4 grey-yellow 160A. Good pollinators have been encountered like 'Golden Clone B', 'Gala', or 'Granny Smith', which are compatible with the observed variety 'Golden Parsi'. The dehisced anther of the 'Golden Parsi' shows a color FAN4 grey-yellow 160A. The undehisced anther of 'Golden Parsi' shows a color FAN4 grey-yellow 160 C.

The pedicel or stalk of the flower is 45+–5 mm long. The pedicel of 'Golden Parsi' is 1.8+–0.1 mm wide when measured at the bottom. The color of the pedicel is FAN4 grey-purple 183A exactly the same as the color of the fruit at a size of 20 mm. Afterwards, the color of the pedicel diminishes and weeks later it turns into a brownish color.

The time of beginning of flowering of 'Golden Parsi' is medium and is similar to that of 'Cox's Orange Pippin' or 'Jonagold'.

The extent of anthocyanin overcolor of a young fruit of 'Golden Parsi' is medium or similar to the extent in 'Idared'.

The size of the fruit of 'Golden Parsi' is medium to large or similar to the size of the fruit of 'Gravensteiner'. The height of the fruit of 'Golden Parsi' is tall and similar to the height in 'Cadel' or 'Iduna.' The diameter of the fruit of 'Golden Parsi' is medium or similar to the diameter of 'Golden Delicious'. The ratio of height of the fruit to diameter of the fruit of 'Golden Parsi' is very large and similar to that of 'Iduna' or 'Priam'. Apples of a 'Golden Parsi' tree have a weight of 240 g+–20 g at a diameter of fruit from 80 to 85 mm. The number of apples per cluster depends on the thinning and the number can be up to 5. The ratio height to width to diameter is large, slightly larger when compared to the 'Golden Delicious', ratio 1.1 to 1 to 1. An apple with a height of 80 mm has a width of 73+–3 mm, and a diameter of 80 mm. Depending on thinning, the normal size of the 'Golden Parsi' fruit is 75 to 85 mm. The general shape of the fruit of 'Golden Parsi' is conic and similar to the shape of 'Jonagold'. The general shape of the fruit of 'Golden Parsi' is conical or similar to the shape of 'Bramley's Seedling' or 'Idared'. Ribbing of the fruit of 'Golden Parsi' is moderate and similar to the ribbing of 'Golden Delicious'. The crowning at the calyx end of the fruit of 'Golden Parsi' is strong or similar to the crowning in 'Red Delicious' (U.S. Plant Pat. No. 2,816).

The size of the eye depression of the fruit of 'Golden Parsi' is medium or similar to the size in 'Cox's Orange Pippin'. The length of the sepal of the fruit of 'Golden Parsi' is short or similar to the length of the sepal of the 'McIntosh'. The 'Golden Parsi' exhibits 5 sepals. The sepals of the 'Golden Parsi' have a length of 4.5+–0.5 mm and a width of 1.8+–0.1 mm measured at bottom. The coloration was FAN3 green 138B. The pedicels of the 'Golden Parsi' tree have a length of 45+–5 mm. The pedicel of the 'Golden Parsi' has a color of FAN3 green 138B. The pedicel of 'Golden Parsi' turns red of color FAN4 grey-purple 183A, exactly as the fruit does at a size of 20 mm. Afterwards, the color diminishes, and some weeks later it turns into a brownish color. The bloom of the skin of the fruit of 'Golden Parsi' is absent or weak or similar to the bloom of the skin of the 'Golden Delicious'.

The depth of the eye basin or calyx depression of the 'Golden Parsi' is medium or similar to the depth in 'Golden Delicious'. The width of the eye basin or calyx depression of the 'Golden Parsi' is medium or similar to the width in 'Golden Delicious'. The eye basin of 'Golden Parsi' is medium open like with 'Golden Delicious'. The opening of the cavity of the calyx of a three year old 'Golden Parsi' tree is from about 2 to 2.5 cm. The ratio of eye basin width to eye basin depth is 2: 1.3+–0.3. The depth of the stalk cavity or stem cavity of the fruit of the 'Golden Parsi' is medium or similar to the depth in 'Golden Delicious'. The stalk cavity is medium open like 'Golden Delicious'. The opening of the cavity of the stem of a 'Golden Parsi' apple of a three year old tree is from about 2.5 to 3 cm. The ratio of width to depth of the stalk cavity of 'Golden Parsi' is 1:1. The width of the stalk cavity of the fruit of 'Golden Parsi' is medium or similar to the width in 'Golden Delicious'. The length of a stalk of an apple fruit of a three year old 'Golden Parsi' tree is 3+–0.5 cm.

The thickness of the stalk of the fruit of 'Golden Parsi' is thin or similar to the thickness in 'Golden Delicious'. The diameter or thickness of the stalk or stem of an apple of a three year old 'Golden Parsi' tree is from about 1.5 to 2.5 mm. The coloration of a 'Golden Parsi' fruit stem is partially FAN4 grey-orange 166A and partially FAN4 grey-orange 166B and different from other 'Goldens'.

A greasiness of the skin of the fruit of 'Golden Parsi' is absent or weak and is similar to the greasiness of the fruit of 'Schone van Boskoop'. The fruit skin of 'Golden Parsi' is very thin, about 0,3 mm. The fruit skin of the 'Golden Parsi' has no tendency to crack. The skin of 'Golden Parsi' differs from the skin of 'Golden Delicious'. The skin of 'Golden Parsi' does not tend to get oily as fast as the skin of 'Golden Delicious' does.

The color of the ground color of the skin of the fruit of 'Golden Parsi' is FAN1 yellow 2A or similar to the color of 'Delorgue', 'Gala', or 'Transparent de Croncels'. The relative area of the overcolor of the fruit of 'Golden Parsi' is small or similar to the area of 'Auralia' or 'Cox's Orange Pippin'. The hue of the over color of the skin of the fruit of 'Golden Parsi' with the bloom removed is FAN1 red 39A or similar to the hue of 'Alkane', 'Galaxy', 'Red Elstar', or 'Regal Prince'. The intensity of the color of the over color of the skin of the fruit of 'Golden Parsi' is medium.

The pattern of over color of the skin of the fruit of 'Golden Parsi' is solid flush with weakly defined stripes or similar to the pattern of 'Galaxy'. The width of the stripes of 'Golden Parsi' are narrow and similar to 'Eden', 'Pinova', or 'Pirella'. The relative area of over color of the fruit of a 'Golden Parsi' tree is small or similar to the area in 'Auralia' or 'Cox's Orange Pippin'. The 'Golden Parsi' fruit expresses a different percentage of over color, depending on altitude. There is 10 percent of over color at sea level. This percentage can go up to 40 percent at 450 m. The pattern of over color of a fruit of 'Golden Parsi' is solid flush with weakly defined stripes or similar to the pattern of 'Obro Gala'.

The area of russet of the fruit of 'Golden Parsi' around the stalk attachment is absent or small or similar to the area of 'Elstar', 'Granny Smith', or 'Piros'. The area of russet around the eye basin of the fruit of 'Golden Parsi' is absent or very low or similar to that of 'Golden Noble'. The area of russet on the cheeks of the fruit of 'Golden Parsi' is absent or very low or similar to 'Golden Noble'. The fruit of the 'Golden Parsi' is resistant and there is no russet. Russet is observed in the stalk cavity of 'Golden Parsi' and assumes 20 to 50 percent of the stalk cavity. The size of the lenticels of the fruit of 'Golden Parsi' is medium or similar to the size in 'Elstar'. The number of the lenticels of the fruit of 'Golden Parsi' is medium or similar to the number of 'Golden Delicious'. The lenticels of the fruit are present in a high number of from about 5 to 8 per square cm without forming a pattern. The diameter of the lenticels of the 'Golden Parsi' fruit are from about 0.1 mm to 0.7 mm. The number of fruit lenticels decreases in a direction toward the calyx to 0 to 5 per square cm and the size of the lenticels decreases to from about 0.05 to 0.2 mm. The color of the lenticels of the 'Golden Parsi' fruit is FAN4 162A.

The length of the stalk of the fruit of 'Golden Parsi' is long or similar to the length with 'Richared Delicious'. The length of a stalk of a 'Golden Parsi' apple of a three year old tree is 3+−0.5 cm. The type of bearing of a 'Golden Parsi' tree is on spurs and long shots. The thickness of the stalk of the fruit of 'Golden Parsi' is thin or similar to the thickness of 'Golden Delicious'. The depth of the stalk cavity of 'Golden Parsi' is medium or similar to the depth of 'Golden Delicious'. The width of the stalk cavity of the fruit of 'Golden Parsi' is medium or similar to that of 'Golden Delicious'. The depth of the eye basin of the fruit of 'Golden Parsi' is medium or similar to the depth of 'Golden Delicious'. The width of the eye basin of the fruit of 'Golden Parsi' is medium or similar to the width of 'Golden Delicious'.

The firmness of the flesh of the fruit of 'Golden Parsi' as measured with a penetrometer is firm like the fruit of a 'Kent' tree. The color of the flesh of the fruit of 'Golden Parsi' is yellowish or similar to the color of 'Delorina' or 'Topaz'. The color of the flesh of the 'Golden Parsi' fruit is FAN1 yellow 11C. The inner quality of 'Golden Parsi' is very much comparable to the one of 'Golden Del Clone B', but significantly different from 'Golden Reinders', according to tests performed by Laimberg Research Station, South Tyrol, Italy. Measurements performed on Sep. 23, 2009 gave the following values for 'Golden Parsi': The starch transition point was 3.7. The Brix—minimum was 14.6. The Brix—maximum was 16.4. The Brix—average was 15.4. The firmness was 8.0. The acidity was 5.2. The juiciness was 20.1. 'Golden Parsi' has 1 degree Brix more sugar when compared to 'Reinders'. 'Golden Parsi' has higher firmness, acidity and juiciness when compared to 'Clone B' and 'Reinders'. The aperture of the locules for a median through locules of the 'Golden Parsi' fruit in cross-section is fully open and similar to the aperture in 'McIntosh'.

The time of fruit harvesting of 'Golden Parsi' is late like the time for 'Golden Delicious' or 'Jonagold'. The harvest time for 'Golden Parsi' is the same as the harvest time for 'Golden Del. Clone B'. 'Golden Parsi' can be harvested 155 days after full bloom for a period of four weeks. Fruit produced per tree depends on the thinning program. The following data were observed for 'Golden Parsi' in Girlan, South Tyrol, Italy: Leaf 2 5 kg; Leaf 3 15 kg; Leaf 4 20 kg. The time of eating maturity of 'Golden Parsi' fruit is late like for 'Golden Delicious'.

The core of the 'Golden Parsi' had a length of 2.5+−0.2 cm and a width of 1.7+−0.1 cm. Locules in a transverse section are partially open and take 25 percent of the total diameter of the core.

The 'Golden Parsi' apple has from about 0 to maximum 13 kernels. The chambers contain up to three kernels. The length of the kernels is from about 7.8 to 9.2 mm. The width of the kernel is about 4.5 mm at the widest point, which occurs at a distance of a third from the heart of the kernel. The width of the kernel at about two thirds of a distance from the heart of a kernel is about 3.7 mm. The thickness of the kernel of 'Golden Parsi' is from about 2.5 to 3 mm. The color of the kernel is FAN4 grey-orange 166C. Stripes or areas with darker color are present at the edges of the kernels and exhibit a darker color FAN4 grey-orange 166A. The interior of the 'Golden Parsi' kernel shows the color FAN4 white N155B.

The winter hardiness and the drought tolerance of the 'Golden Parsi' are the same as the winter hardiness and drought tolerance of the 'Golden Delicious'. The 'Golden Parsi' plant is sensitive to the plant disease scabs. The 'Golden Parsi' plant is moderately resistant to fire blight. Diseases of the 'Golden Parsi' fruit include sensitivity to bruising and fruit shriveling in storage.

The colors of the written description override the colors of the pictures. The colors were compared with The Royal Horticultural Society Color Chart, publication year 2001, in the following.

A comparison was performed between 'Golden Reinders' and 'Golden Clone B' and 'Golden Parsi'. The Color Chart used in this specification is The Royal Horticultural Society Colour Chart, publication year 2001.

The color for a one-year-old shoot was FAN4 (grey-brown) N199A for 'Golden Reinders', FAN4 (grey-brown) N199A for 'Golden Clone B', and FAN4 (grey-brown) N199B for 'Golden Parsi'. The color of the stem was FAN4 (grey-brown) N199A for 'Golden Reinders', FAN4 (grey-brown) N199A for 'Golden Clone B', and FAN4 (grey-brown) N199B for 'Golden Parsi'. The color of the upper side of the leaf was FAN3 (yellow-green) 147A for 'Golden Reinders', FAN3 (yellow-green) 147A for 'Golden Clone B', and FAN3 (green) 139A for 'Golden Parsi'. The leaf blade is dark green, as FAN3 (green) 139A clearly shows a dark green color. The 'Golden Parsi' leaf is darker than the leaves of other 'Goldens'. The color of the fruit stem was FAN4 (grey-orange) 166C for 'Golden Reinders', FAN4 (grey-orange) 166C for 'Golden Clone B', and FAN4 (grey-orange) 166A for 'Golden Parsi'.

An overcolor or blush was absent from the fruits of 'Golden Reinders' and from 'Golden Clone B'. A blush appears early in the season in June on the fruit of 'Golden Parsi' with a color FAN4 (grey-red) 179B. The blush disappears almost totally, and towards harvest increases and gets red on the fruit of 'Golden Parsi'. The blush remains red even after months of storage of the 'Golden Parsi' apple. The color of the overcolor of the 'Golden Parsi' fruit is FAN1 (red) 39A. The crowning of the fruit at the calyx end is small for 'Golden Clone B' and is very dominant for 'Golden Parsi'. The russet of the fruit is medium for 'Golden Reinders', is high for 'Golden Clone B', and is absent or very low for 'Golden Parsi'. The russet around the stalk cavity of the fruit is medium for 'Golden Clone B' and is absent or very low for 'Golden Parsi'. The russet around the eye basin of the fruit is medium for 'Golden Clone B' and is absent or very low for 'Golden Parsi'. The russet on the cheeks of the fruit is medium for 'Golden Clone B' and is absent or very low for 'Golden Parsi'.

The invention claimed is:

1. A new and distinct variety of a 'Golden Parsi' apple tree, *Malus domestica*, substantially as shown and described.

* * * * *

UNITED STATES PATENT AND TRADEMARK OFFICE

CERTIFICATE OF CORRECTION

PATENT NO. : PP22,859 P3
APPLICATION NO. : 12/798834
DATED : July 17, 2012
INVENTOR(S) : Egon Schmider and Thomas Braun It is certified that error appears in the above-identified patent and that said Letters Patent is hereby corrected as shown below:

Title Page item (73) Assignee, should read: KIKU SRL - GmbH

Signed and Sealed this
Ninth Day of April, 2013

Teresa Stanek Rea
*Acting Director of the United States Patent and Trademark Office*